United States Patent [19]

Hawkins et al.

[11] Patent Number: 5,270,451
[45] Date of Patent: Dec. 14, 1993

[54] EXTRACTION METHOD FOR PREPARING THROMBOPLASTIN REAGENTS

[75] Inventors: Pamela L. H. Hawkins; James R. Maynard, both of Miami, Fla.

[73] Assignee: Baxter Diagnostics Inc., Deerfield, Ill.

[21] Appl. No.: 926,134

[22] Filed: Aug. 6, 1992

Related U.S. Application Data

[63] Continuation of Ser. No. 276,083, Nov. 23, 1988, abandoned.

[51] Int. Cl.$^5$ .......................... C07K 3/02; C07K 3/74; C07K 13/00
[52] U.S. Cl. ...................................... 530/381; 530/384
[58] Field of Search ................................ 530/381, 384

[56] References Cited

U.S. PATENT DOCUMENTS

| | | | |
|---|---|---|---|
| 2,847,350 | 8/1958 | Singher et al. | 530/381 |
| 3,862,314 | 1/1975 | Zwisler et al. | 530/381 |
| 3,980,432 | 9/1976 | Trobisch et al. | 435/13 |
| 3,983,004 | 9/1976 | Trobisch et al. | 436/8 |
| 4,416,812 | 11/1983 | Becker et al. | 530/381 |
| 4,755,461 | 4/1986 | Lawson | 435/13 |
| 5,017,556 | 5/1991 | O'Brien et al. | 530/381 |
| 5,219,995 | 6/1993 | Herring et al. | 530/381 |

FOREIGN PATENT DOCUMENTS 3150596 12/1981 Fed. Rep. of Germany ... 260/112 R

OTHER PUBLICATIONS

Guha et al. (1986, Jan.) Proc. Natl. Acad. Sci. U.S.A. 83:299-302.
Y. Hatefi, W. G. Hanstein "Destabilization of Membranes with Chaotropic Ions" General Methodoloyg, Method in Enzymology, 1974, vol. XXXI, p. 770.
R. M. Howee, G. B. D. Scott "The Role of Lipoproteins in the Production of Hypercoagulability: A New Concept" British Journal of Experimental Pathology vol. XLV, No. 6, p. 618.
Neville W. Spurling, Janet Savory "The Influence of Residual Factor VII on the Sensitivity of Brain Thromboplastin" Thrombos. Haemostas, 1978, vol. 39, p. 592.
Joyce E. Gardiner, Roy M. Howerll "Partial Purification of a Naive Form of Thromboplastin From Porcine Brain" Biochemical Society Transactions, 1980, vol. 8, p. 133.

Primary Examiner—Robert A. Wax
Assistant Examiner—William W. Moore
Attorney, Agent, or Firm—Louise S. Pearson; Cynthia G. Tymeson

[57] ABSTRACT

The Prothrombin Time (PT) is used as a screening test for blood coagulation factor deficiencies and for monitoring oral anti-coagulant therapy using coumadin. Thromboplastin reagents activate the extrinsic pathway of coagulation and are the basis for the Prothrombin Time (PT) test. This invention describes the use of barium sulfate and chaotropic agents, and nonionic detergents, for the extraction of sensitive thromboplastin reagents from tissue. Extraction with sodium thiocyanate alone also greatly enhances thromboplastin sensitivity. This invention should be useful for all thromboplastins and will improve their sensitivity for all PT-based tests and specific assays.

15 Claims, No Drawings

EXTRACTION METHOD FOR PREPARING THROMBOPLASTIN REAGENTS

This is a continuation of application Ser. No. 07/276,083, filed on Nov. 23, 1988, now abandoned.

FIELD OF THE INVENTION

This invention relates to an improved method of extracting and preparing thromboplastin reagents.

BACKGROUND OF THE INVENTION

Thromboplastin reagents activate the extrinsic pathway of coagulation and are the basis for the prothrombin time (PT) test. The PT test is used to screen for blood coagulation factor deficiencies and for monitoring oral anticoagulant therapy (e.g. coumadin). Reagents for PT tests include tissue thromboplastin, also called tissue factor, and calcium ions as active ingredients diluted with appropriate buffers and stabilizers. Thromboplastin forms a complex with coagulation factor VII to greatly enhance its proteolytic activity.

Thromboplastin may be derived from a variety of tissues of different animal sources. Each tissue has a characteristic activity and sensitivity to coagulation enzymes (i.e., factors); these properties are modulated by other constituents of the reagent. Thromboplastin sensitivity is defined as the prolongation of the clotting times of both coumadinized plasmas and plasmas deficient in clotting factors II, V, VII, and X. Sensitivity to coumadinized plasma is assessed by taking the ratio of an abnormal plasma sample to a normal plasma sample.

Currently, the most sensitive thromboplastin reagents are derived from human brain and placenta. The limited availability of these materials, their cost and the potential for HIV virus contamination limit their universal acceptance. Thromboplastins derived from rabbit brain, the most common source, typically have relatively low sensitivity compared to thromboplastins derived from human tissues. The source of the thromboplastin, the method of extracting the thromboplastin and the reagent composition are all important parameters in determining reagent sensitivity. Variations in the composition of PT reagents can also be used to improve stability and adjust clotting times of plasma samples from normal individuals.

Historically thromboplastin has been extracted from tissues by heating the tissue in water or saline solutions. Thromboplatin reagents made by Baxter Healthcare Corporation, Dade Division, contain thromboplastins extracted in saline-tartrate solutions (U.S. Pat. No. 3,522,148—Jul. 25, 1970). These extracts are centrifuged to remove large particles. The supernate thromboplastin extract contains the active thromboplastin along with the sodium chloride and sodium tartrate from the extraction fluid. In Thromboplastin C the thromboplastin extract is added to a solution containing calcium lactate, sodium chloride, sodium tartrate, glycine and carboxymethyl cellulose. The final concentration of extract is 25% of the final reconstituted volume. In Thromboplastin FS, the thromboplastin extract is added to a solution containing imidazole, calcium lactate, sodium chloride, sodium tartrate, glycine and carboxymethyl cellulose. Because the final concentration of extract is 50% of the final reconstituted volume, Thromboplastin FS (TPES) made by Baxter Healthcare Corporation, Dade Division, has a relatively high concentration of rabbit brain extract. While more sensitive than other rabbit brain thromboplastins, the normal range PT values are longer than desired, the turbidity is high and the stability is less than optimal.

Boehringer Mannheim has developed a process to make rabbit brain thromboplastin more sensitive (DE 3150594A1). In their procedure, rabbit brain powder is mixed with equal parts of cellulose powder and washed with sodium acetate buffer at pH 6.5-8 to remove contaminants such as hemoglobin. The brain residue is then extracted with surface active agents, such as sodium deoxycholate in the presence of calcium ions. The key constituent disclosed in the Boehringer Mannheim process is calcium ions, and, if needed, a surface active agent is used. The use of barium sulfate is discussed in the Boehringer Mannheim patent, but discounted: "according to our own experiences, the thromboplastin largely co-precipitates with the barium sulfate." In conventional procedures the relative insensitivity of thromboplastins is due, in part, to the presence of coagulation factor VII, being tightly bound to the thromboplastin. Barium sulfate is commonly used as an adsorbing agent to remove vitamin K-dependent coagulant proteins such as factors II, VII, IX, and X.

BRIEF SUMMARY OF THE INVENTION

The present invention uses various combinations of nonionic detergents, such as Triton, ® X-100, chaotropic ions such as thiocyanate, iodide, guanidine and perchlorate, and barium sulfate to extract thromboplastin from a tissue source. Nonionic detergents greatly enhance the efficiency of removing the coagulation factors bound to the thromboplastin. The approach described herein offers the advantage of enhanced sensitivity to factor deficiencies and coumadin therapy while maintaining a relatively short normal range PT. A survey conducted by the CAP Hematology Resource Committee in 1978 revealed that the normal range PT was 9-15 seconds for 96% of the laboratories reporting (Triplett, D. A., "How the Prothrombin Time Actually is Performed" in *Standardization of Coagulation Assays: An Overview*, ed. by D. A. Triplett, College of American Pathologists, Skokie, 1982, pp. 113-119). The preferred PT range for normal donors is 10-14 seconds. Reagents prepared using the methods described here have enhanced reconstituted stability over Thromboplastin FS, use less brain extract and are less optically dense. The present invention allows sensitivity to Factor VII deficient plasma using insensitive thromboplastin reagents to be set at any PT; the preferred PT time for Factor VII deficient plasma is greater than sixty seconds. The thromboplastin reagent of the present invention will have a ratio of the abnormal control (COL2) to the normal control (COL1) greater than 1.8, however, preferably the ratio is in the range of 1.8 to 3.0.

Alternatively, chaotropic ions, such as thiocyanate, guanidine, or iodide, used alone in the extraction fluid greatly enhance sensitivity. Chaotropic ions are agents used in disrupting membranes and enzyme complexes by breaking noncovalent forces. (W. Hanstein, *Destabilization of Membranes with Chaotropic Ions*, Meth. Enzy. XXXI (1974)). Chaotropic ions typically have a low charge density with a large radius. Commonly used ions include: tribromoacetate, trichloroacetate, quanidinium, thiocyanate, iodide, perchlorate, dichloroacetate, nitrate, bromide, trifluoroacetate and chloroacetate.

DETAILED DESCRIPTION AND BEST MODE

In this invention tissue, such as acetone-dehydrated rabbit brain powder, is extracted with a combination of barium sulfate, nonionic detergents and chaotropic ions, such as thiocyanate, iodide, guanidine or perchlorate, to control reagent properties. This invention should be useful for all thromboplastins and will improve the sensitivity for all PT-based tests and specific assays.

PT values can be determined using automated coagulation analyzers, such as the MLA Electra 800, mechanical instruments, such as Fibrometers, or by manual techniques. The abnormal plasma for these studies has been either an abnormal control such as Baxter Healthcare Corporation, Dade Division, Ci-Troll ® Level II (COL2) or lyophilized coumadinized plasmas (LAC) for an anticoagulant control. Ci-Trol ® Level I (COL1) or a pool of fresh normal citrated plasma (FNP) have been used to determine normal PT values. Sensitivity to factor deficiencies is assessed by measuring the PT of a factor VII-deficient plasma (CF7). Rabbit brain thromboplastins available in the United States (Dade Thromboplastin C) yield ratios of 1.5 for COL2/COL1 and a 28-30 sec PT for factor VII-deficient plasma on the MLA Electra 800.

EXAMPLE I: GENERAL PROCESS USED TO PREPARE THROMBOPLASTINS

To make the thromboplastin reagent, rabbit brain power (50 gm) is extracted in an extraction fluid (1000 mL) containing sodium chloride (30-180 mM), a nonionic detergent, such as Triton ® X-100 (0.01-0.25%) and a chaotropic ion, such as sodium thiocyanate (5-100 mM). Alternatively, the extraction fluid may contain only b sodium chloride (0-150 mM) and the chaotropic ion (5-100 mM). Barium sulfate powder is added to the extraction fluid at 0.1-1.0 gm/gm brain powder. The extraction is performed at 43 to 470° C. for fifteen (15) minutes; the extraction mixture is then centrifuged for ten (10) minutes at 2500 RPM to remove the barium sulfate and large particles. The extract is added to a base containing calcium ions (7-14 mM), sodium chloride (70-150 mM), buffers and stabilizers. The product is then freeze-dried.

EXAMPLE II: THE EFFECT OF TRITON X-100 AND BARIUM SULFATE IN EXTRACTION ON THROMBOPLASTIN SENSITIVITY

Acetone-dehydrated rabbit brain powder (1 gm) was extracted in 20 mL of 0.63% sodium chloride (NaCl) containing 0.6 gm of barium sulfate (BaSO$_4$) and 0-0.25% Triton X-100 ® (Rohm & Haas, Philadelphia, Pa.) for fifteen (15) minutes at 45° C.; the extraction mixture was then centrifuged at 2500 RPM for ten (10) minutes to remove the barium sulfate and large particles. The extract was added to a base at a final concentration of 32% in 30 mM (TAPSO) buffer, 5% glycine, 0.6% polyethylene glycol (PEG) with a molecular weight of 8000, 13.7 mM calcium chloride (CaCl$_2$), 100 mM NaCl, pH 7.0. Prothrombin times (PT) in seconds were recorded using an MLA Electra 800. (Medical Laboratory Automation, Pleasantville, N.Y.)

Both the ratio of COL2/COL1 and PT of factor VII-deficient plasma (CF7) increase substantially as the amount of detergent is increased (Table I).

TABLE I

Effect of Triton X-100 and Barium Sulfate in Extraction on Thromboplastin-bulk (MLA-800): Average of 2 replicates

| % Triton X-100 | COL1 | COL2 | RATIO COL2/COL1 | CF7 |
|---|---|---|---|---|
| 0% Control | 11.8 | 20.6 | 1.75 | 95.9 |
| 0.05% | 12.1 | 22.1 | 1.83 | 107.4 |
| 0.1% | 13.0 | 25.1 | 1.93 | 120.4 |
| 0.25% | 14.3 | 34.4 | 2.41 | 193.4 |

Base Formulation:
30 mM TAPSO, 5% Glycine, 0.6% PEG, 13.7 mM CaCl$_2$, 100 mM NaCl, 32% Extract, pH 7.0
Brain extracted in 0.63% NaCl and detergent with barium sulfate at 0.6 gm/gm brain in 20 mL of extraction fluid

EXAMPLE III: THE EFFECT OF SODIUM THIOCYANATE (NaSCN) IN EXTRACTION ON THROMBOPLASTIN SENSITIVITY

Acetone-dehydrated rabbit brain powder (1 gm) was extracted in 20 mL of 0.63% sodium chloride (NaCl), except where noted, containing 0 (control), 10, 50, and 100 mM NaSCN for fifteen (15) minutes at 45° C.; a sample containing 100 mM NaSCN, without NaCl was also evaluated. Barium sulfate was not used in this experiment. The extraction mixture was centrifuged as described in Example I. Prothrombin times (PT) in seconds were recorded using an MLA Electra 800.

Both the ratio of- COL2/COL1 and PT of factor VII-deficient plasma (CF7) increase substantially as the amount of NaSCN is increased (Table II). Sodium thiocyanate alone increased thromboplastin sensitivity.

TABLE II

Effect of Sodium Thiocyanate (NaSCN) in Extraction on Thromboplastin - bulk (MLA-800)

| | COL1 | COL2 | RATIO COL2/COL1 | CF7 |
|---|---|---|---|---|
| CONTROL | 11.9 | 21.5 | 1.81 | 37.3 |
| 10 mM NaSCN | 12.5 | 24.1 | 1.93 | 67.4 |
| 50 mM NaSCN | 13.7 | 30.9 | 2.26 | 159.3 |
| 100 mM NaSCN | 14.7 | 35.6 | 2.42 | 177.7 |
| 100 mM NaSCN-NO NaCL | 14.1 | 31.6 | 2.24 | 131.6 |

Base Formulation:
30 mM TAPSO, 5% Glycine, 0.6% PEG, 13.7 mM CaCl$_2$, 100 mM NaCl, 32% Extract, pH 7.0

EXAMPLE IV: COMPARISON OF VARIOUS COMPOSITIONS OF EXTRACTION FLUIDS AND PERCENTAGE OF EXTRACT ON THROMBOPLASTIN SENSITIVITY

Rabbit brain powder was extracted in extraction fluids containing two (2) different compositions of NaCL, Triton X-100, NaSCN and barium sulfate. In Table III, Extract E contained 130 mM NaCl, 50 mM NaSCN, 0.05% Triton X-100 and 0.3 gm barium sulfate/gm brain powder; Extract N contained 50 mM NaCl, 10 mM NaSCN, 0.02% Triton X-100 and 0.4 gm barium sulfate/gm brain powder. The brain powder was extracted, centrifuged and the extracts were added to a base to the final concentrations of 32% or 50% as described in Example I. Prothrombin Times (PT) in seconds were recorded using an MLA Electra 800.

Table III shows that the components of the extraction fluids and the amount of extract can vary considerably to yield thromboplastins with enhanced sensitivity over rabbit brain thromboplastins, such as Dade Thromboplastin C (ratio COL2/COL1 = 1.5).

TABLE III

Comparison of Various Compositions of Extraction Fluids and Percentage of Extract on Thromboplastin - Bulk (MLA-800)

| % Extract | COL1 | COL2 | RATIO COL2/COL1 | FNP | LAC | RATIO LAC/FNP | CF7 |
|---|---|---|---|---|---|---|---|
| 32% Extract E | 14.6 | 32.8 | 2.25 | 14.2 | 35.5 | 2.50 | 81.1 |
| 50% Extract E | 16.9 | 45.5 | 2.69 | 15.8 | 50.4 | 3.19 | 155.1 |
| 32% Extract N | 12.8 | 24.1 | 1.88 | 12.4 | 27.4 | 2.23 | 106.9 |
| 50% Extract N | 13.9 | 32.3 | 2.32 | 13.4 | 39.0 | 2.91 | 176.6 |
| Thromboplastin FS | 13.3 | 24.5 | 1.84 | 13.0 | 31.4 | 2.42 | 64.6 |

Base Formulation:
30 mM TAPSO, 5% Glycine, 0.6% PEG, 13.7 mM CaCl$_2$, 100 mM NaCl, pH 7.0
Extract E:
Brain Powder extracted in 130 mM NaCl, 50 mM NaSCN, 0.05% Triton X-100, 0.3 gm barium sulfate/gm brain powder
Extract N:
Brain Powder extracted in 50 mM NaCl, 10 mM NaSCN, 0.02% Triton X-100, 0.4 gm barium sulfate/gm brain powder

EXAMPLE V: COMPARISON OF VARIOUS FORMULATIONS OF SENSITIVE THROMBOPLASTINS

Acetone-dehydrated rabbit brain powder was extracted in a solution containing 50 mM NaCl, 10 mM NaSCN, 0.02% Triton X-100 and 0.4 gm barium sulfate/gm brain powder. The brain powder was extracted as described in Example I. The extracts were added to bases for two (2) different formulations: Formulation D contained 35% extract in 40 mM bicine buffer, 5.25% glycine, 0.6% PEG, 10 mM CaCl$_2$, 134 mM NaCl, pH 7.1: Formulation T contained 36% extract in 80 mM TAPSO, 5.25% glycine, 0.6% PEG, 10 mM CaCl$_2$, 118 mM NaCl, pH 7.4. Both formulations were lyophilized. After reconstitution, PT in seconds was recorded using an MLA Electra 800.

Table IV shows that the composition of the formulation can vary considerably to yield thromboplastins with enhanced sensitivity and other properties superior to Thromboplastin FS, a relatively sensitive rabbit brain thromboplastin.

EXAMPLE VI: PREPARATION OF THROMBOPLASTINS WITH SENSITIVITY TYPICAL OF THOSE SOLD IN THE U.S.

Acetone-dehydrated rabbit brain powder was extracted in solution containing 50 mM NaCl, 10 mM NaSCN, 0.02% Triton X-100 and 0.4 gm barium sulfate/gm brain powder. The brain powder was extracted as described in Example 1. The extracts were added to bases for three different formulations: Formulation E contained 10% extract in 53 mM TAPSO buffer, 4.00% glycine, 0.3% PEG, 11 mM CaCl$_2$, 50 mM NaCl, pH 7.4; Formulation F contained 12% extract in 50 mM TAPSO buffer, 4.00% glycine, 0.3% PEG, 11 mM CaCl$_2$, 50 mM NaCl, pH 7.4; Formulation G contained 10% extract in 53 mM TAPSO buffer, 4.00% glycine, 0.3% PEG, 11 mm CaCl$_2$, 65 mM NaCl, pH 7.4. The formulations were lyophilized. After reconstitution, PT in seconds were records using an MLA Electra 800.

Table V shows that the extraction fluids described herein can be used to make conventional rabbit brain thromboplastins available in the U.S. similar to Thromboplastin C. Relatively small amounts of extract (10-12% versus 25% for Thromboplastin C) are required to make a thromboplastin with lower COL/COL1 ratio and LAC/FNP ratio. However, the sensitivity to factor VII is enhanced.

TABLE IV

Comparison of Various Formulations of Sensitive Thromboplastins - Bulk (MLA-800)

| Formulation | COL1 | COL2 | RATIO COL2/COL1 | FNP | LAC | RATIO LAC/FNP | CF7 |
|---|---|---|---|---|---|---|---|
| D | 13.4 | 31.1 | 2.32 | 12.4 | 33.5 | 2.70 | 86.3 |
| T | 14.0 | 35.0 | 2.50 | 13.0 | 33.9 | 2.61 | 93.0 |
| Thromboplastin FS | 14.2 | 26.7 | 1.88 | 13.4 | 30.5 | 2.28 | 58.9 |

Extract Mixture:
Brain Powder extracted in 50 mM NaCl, 10 mM NaSCN, 0.02% Triton X-100, 0.4 gm barium sulfate/gm brain powder
Formulation D:
40 mM Bicine, 5.25% Glycine, 0.6% PEG, 10 mM CaCl$_2$, 134 mM NaCl, pH 7.1
Formulation T:
80 mM TAPSO, 5.25% Glycine, 0.6% PEG, 10 mM CaCl$_2$, 118 mM NaCl, pH 7.4

TABLE V

Comparison of Various Formulations of Thromboplastins with Sensitivity Typical of those sold in the U.S. (MLA-800)

| Formulation | COL1 | COL2 | RATIO COL2/COL1 | FNP | LAC | RATIO LAC/FNP | CF7 |
|---|---|---|---|---|---|---|---|
| E | 11.8 | 20.4 | 1.73 | 11.6 | 21.7 | 1.87 | 42.1 |
| F | 11.7 | 20.4 | 1.74 | 11.3 | 21.3 | 1.88 | 40.6 |
| G | 11.4 | 19.7 | 1.73 | 11.1 | 21.0 | 1.89 | 40.4 |

TABLE V-continued

Comparison of Various Formulations of Thromboplastins with Sensitivity Typical of those sold in the U.S. (MLA-800)

| Formulation | COL1 | COL2 | RATIO COL2/COL1 | FNP | LAC | RATIO LAC/FNP | CF7 |
| --- | --- | --- | --- | --- | --- | --- | --- |
| Thromboplastin C | 11.9 | 20.2 | 1.70 | 11.5 | 20.2 | 1.76 | 27.7 |

Extract Mixture:
Brain Powder extracted in 50 mM NaCl, 10 mM NaSCN, 0.02% Triton X-100, 0.4 gm barium sulfate/gm brain powder
Formulation E:
10% Extract, 53 mM TAPSO, 4.00% Glycine, 0.3% PEG, 11 mM $CaCl_2$, 50 mM NaCl, pH 7.4
Formulation F:
12% Extract, 50 mM TAPSO, 4.00% Glycine, 0.3% PEG, 11 mM $CaCl_2$, 50 mM NaCl, pH 7.4
Formulation G:
12% Extract, 50 mM TAPSO, 4.00% Glycine, 0.3% PEG, 11 mM $CaCl_2$, 65 mM NaCl, pH 7.4

VARIANTS OR EQUIVALENTS OF THE INVENTION

The performance and sensitivity of a PT reagent is the result of interactions between all of the constituents of the reagent. Generally, changes in formulation which increase the sensitivity also increase the value of the normal PT. In the present invention, the components of the extraction fluid are carefully balanced for best normal PT and sensitivity. In addition, the individual constituents of the extraction mixture influence reagent performance in specific ways. Varying the concentrations of the various components also alters the properties of the prepared extract; therefore, extracts with different properties can be prepared depending on the extraction fluid composition.

Barium sulfate and any nonionic detergent, such as Triton ® X-100, Brij-35, Nonidet ® P40, FSN ® and Tergitol ® greatly enhance sensitivity, especially to specific coagulation factor deficiencies such as factor VII. Chaotropic ions (thiocyanate, guanidine, iodide, perchlorate) alone in the extraction enhances sensitivity to both coumadinized patient samples and specific factor deficiencies such as factor VII. To make the thromboplastin reagent, the tissue is extracted in an extraction fluid containing sodium chloride (30-180 mM), the nonionic detergent (0.01-0.25%) and the chaotropic ion such as thiocyanate, guanidine, iodide and perchlorate (5-100 mM). Barium sulfate powder is added to the extraction fluid at 0.1-1.0 gm/gm brain powder. Alternatively, the extraction fluid may contain only sodium chloride (0-150 mM) and sodium thiocyanate (5-100 mM). The extraction is performed at 43° to 47° C. for fifteen (15) minutes; the extraction mixture is then centrifuged for ten (10) minutes at 2500 RPM to remove the barium sulfate and large particles. The extract is added to a base containing calcium ions (7-14 mM), sodium chloride (70-150 mM), buffers and stabilizers. The buffers and stabilizers can be varied to improve the stability of the product as well.

The extraction method and components can be used with any source of tissue containing thromboplastin, such as rabbit brain and lung, bovine brain and lung, ovine brain and lung, and human brain, lung and placenta.

What is claimed is:

1. A method for extracting thromboplastins comprising:
   (a) contacting tissue containing thromboplastin with an effective amount of extraction fluid comprising about 0.1 to 1.0 gram of barium sulfate per gram of tissue, about 0.01 to 0.25% of a nonionic detergent, about 5 to 100 mM chaotropic ion, and a salt thereby extracting thromboplastin into the fluid, and
   (b) separating said extracted thromboplastin from said depleted tissue and barium sulfate.

2. The method of claim 1 wherein the effective amount of said extraction fluid is about 100 mL for every 5 grams of tissue.

3. The method of claim 1 wherein the concentration of the salt is about 30-180 mM.

4. The method of claim 1 wherein the extraction is conducted at between 43° to 47° C. for approximately fifteen minutes.

5. The method of claim 1 wherein the tissue is rabbit brain powder.

6. The method for extracting thromboplastin reagents comprising:
   (a) contacting tissue containing thromboplastin with an effective amount of extraction fluid comprising about 0.1 to 1.0 gram of barium sulfate per gram of tissue, about 0.01 to 0.25% nonionic detergent and a salt, thereby extracting thromboplastin into the fluid, and
   (b) separating said extracted thromboplastin from said depleted tissue and barium sulfate.

7. The method of claim 6 wherein the effective amount of said extraction fluid is about 100 mL for every 5 grams of tissue.

8. The method of claim 6 wherein the extraction is conducted at between 43° to 47° C. for approximately fifteen minutes.

9. The method of claim 6 wherein said tissue is rabbit brain powder.

10. The method of claim 6 wherein the concentration of the salt is between 30-180 mM.

11. A method for extracting a thromboplastin reagent comprising:
    (a) contacting tissue containing thromboplastin with an effective amount of extraction fluid comprising a salt, about 5 to 100 mM of a chaotropic ion, and about 0.1 to 1.0 grams of barium sulfate per gram of tissue, thereby extracting thromboplastin into the fluid, and
    (b) separating said extracted thromboplastin from said depleted tissue and barium sulfate.

12. The method of claim 11 wherein the concentration of the salt is about 30-180 mM.

13. The method of claim 11 wherein the extraction is conducted at between 43°-47° C. for approximately fifteen minutes.

14. The method of claim 11 wherein the effective amount of said extraction fluid is about 100 mL for every 5 grams of tissue.

15. The method of claim 11 wherein said tissue is rabbit brain powder.

* * * * *